United States Patent
DuPont

(10) Patent No.: US 9,701,827 B2
(45) Date of Patent: Jul. 11, 2017

(54) X-RAY OPAQUE POLYMERIC GASKET

(75) Inventor: Paul Robert DuPont, Newton, NJ (US)

(73) Assignee: Garlock Hygienic Technologies, LLC, Charlotte, NC (US)

(*) Notice: Subject to any disclaimer, the term of this patent is extended or adjusted under 35 U.S.C. 154(b) by 346 days.

(21) Appl. No.: 13/298,507

(22) Filed: Nov. 17, 2011

(65) Prior Publication Data

US 2012/0121066 A1 May 17, 2012

Related U.S. Application Data

(60) Provisional application No. 61/414,552, filed on Nov. 17, 2010.

(51) Int. Cl.
| | |
|---|---|
| *G01N 23/10* | (2006.01) |
| *C08L 23/16* | (2006.01) |
| *C08L 83/04* | (2006.01) |
| *C08K 3/08* | (2006.01) |
| *C08K 3/30* | (2006.01) |

(52) U.S. Cl.
CPC ............ *C08L 23/16* (2013.01); *C08K 3/08* (2013.01); *C08K 3/30* (2013.01); *C08L 83/04* (2013.01); *G01N 23/10* (2013.01); *C08K 2003/3045* (2013.01); *C08K 2201/01* (2013.01)

(58) Field of Classification Search
CPC ........ C08L 23/16; G01N 23/04; G01N 23/10; C08K 2003/3045
See application file for complete search history.

(56) References Cited

U.S. PATENT DOCUMENTS

| | | | | |
|---|---|---|---|---|
| 3,143,512 A | * | 8/1964 | Kline | ............................ 252/478 |
| 3,956,631 A | * | 5/1976 | Crosby, Jr. | ...................... 378/58 |
| 4,196,886 A | * | 4/1980 | Murray | ...................... F16K 1/38 |
| | | | | 251/357 |
| 4,568,115 A | | 2/1986 | Zimmerly | |
| 4,879,734 A | * | 11/1989 | Schreckendgust et al. | .... 378/57 |
| 5,045,594 A | * | 9/1991 | Samuel et al. | .................. 525/57 |
| 6,318,576 B1 | | 11/2001 | Graham et al. | |
| 7,390,580 B1 | * | 6/2008 | Dupont | ...................... 428/692.1 |
| 2005/0211930 A1 | * | 9/2005 | DeMeo | ................ G01V 5/0008 |
| | | | | 250/516.1 |
| 2009/0326114 A1 | * | 12/2009 | Grothe et al. | ................. 524/148 |
| 2013/0303680 A1 | * | 11/2013 | Weaver | ................... C08L 53/00 |
| | | | | 524/528 |

OTHER PUBLICATIONS

"Metal Detection, Checkweighing and X-ray Inspection from Loma Systems", retrieved from internet on Oct. 19, 2010, <URL:http://www.loma.com>.

* cited by examiner

*Primary Examiner* — Dani Fox

(74) *Attorney, Agent, or Firm* — Maine Cernota & Rardin

(57) ABSTRACT

A system is provided for the detection of contaminant particulates in closed containers, that system having a plurality of system components susceptible to degradation during the manufacture of container contents and filling of the closed containers, the system components susceptible to degradation comprising a radio opaque composition of matter; an x-ray source disposed proximate to a path of the closed container in a production line; an x-ray image intensifier whereby x-rays from the x-ray source are collected and an image is generated; a ccd camera whereby the x-ray image is digitized; a contaminated container rejection mechanism whereby closed containers having x-ray images with radio opaque portions are rejected as contaminated and removed from the production line.

5 Claims, 4 Drawing Sheets

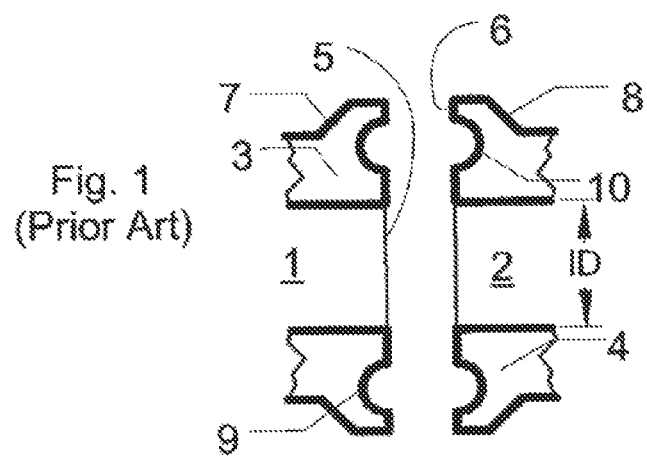
Fig. 1
(Prior Art)
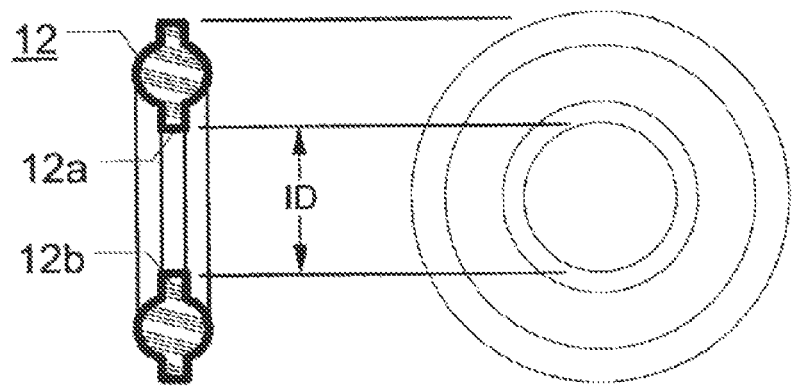
Fig. 2
(Prior Art)
Fig. 3
(Prior Art)
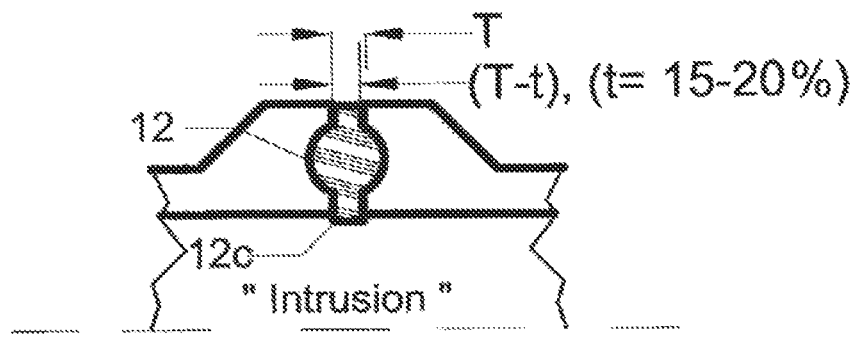
Fig. 4
(Prior Art)

X-RAY OPAQUE POLYMERIC GASKET

RELATED APPLICATIONS

This application claims the benefit of U.S. Provisional Application No. 61/414,552, filed Nov. 17, 2011. This application is herein incorporated by reference in its entirety for all purposes.

FIELD OF THE INVENTION

This invention relates to sanitary fittings for pipes of the type employed in the food processing and pharmaceutical industries and, more particularly, to gaskets, valves and valve seats employing compressible elastomeric materials for sealing said pipes against leakage of the fluids carried therethrough.

BACKGROUND OF THE INVENTION

Plants processing foods, pharmaceuticals, biological and technological fluid materials generally require fluid piping systems that must be free from voids and crevices to prevent accumulations of materials, that can readily be taken apart for periodic cleaning and that can withstand the application of CIP (clean in place) solutions and steam cycles used for cleaning. The gasket material used at joints in the piping systems must have appropriate resiliency and resistance against deterioration by the chemical and physical characteristics of the fluids under the conditions of temperature and pressure occurring during sanitization, such as the use of 15 psi saturated steam, hot, de-ionized water or hot WFI (water for injection).

As compared to a general use gasket, the material for a sanitary-pipe gasket to be used in manufacturing medicines, foods, etc. must be more carefully selected. This requirement is made to prevent contamination of products by components of the gasket material eluting into the fluid transported through the piping. Accordingly, many sanitary-pipe gaskets have conventionally been formed of silicone rubber which has excellent heat resistance and chemical resistance. Other materials employed in food and pharmacological processing include ethylene propylene diene monomer (EPDM), buna rubber, and fluoroelastomers such as Viton® or FKM 615A™. A dipolymer of vinylidene fluoride and hexafluoroproplyene often used as base elastomers for seals, spacers and gaskets employed in sanitary piping systems.

A pair of known pipe ends equipped with sanitary pipe flange fittings 1, 2 is shown in FIG. 1. Sanitary pipe fittings 1, 2 have flanges 3, 4 with substantially flat facing faces 5, 6 each of which has a recess or annular groove 9, 10 that is designed to accommodate sealing gasket. Typically, a simple O-ring gasket (not shown) or preferably, an O-ring 12, FIGS. 2, 3, fitted with peripheral flat, compressible sections 12a, 12b of elastomeric material, such as shown in U.S. Pat. No. 6,318,576 which is herein incorporated by reference, may be used. Let it be assumed that the original thickness of portions 12a, 12b is "T".

The pipe fittings are made-up by tightening the screw (not shown) of a conventional hinged clamp (not shown, but see U.S. Pat. No. 4,568,115 which is herein incorporated by reference). The hinged clamp exerts a camming action on the exterior beveled shoulders 7, 8 of flanges 3, 4 forcing flat faces 5, 6 against each other and compressing the gasket 12 (FIG. 2) between them.

Unfortunately, as shown in FIG. 4, if the clamp is tightened too much in an effort to prevent leakage at the joint, the gasket 12 will be unduly compressed causing a portion 12c of gasket 12 to be extruded into the interior lumen ID at the joint between pipes 1, 2. Empirical data tends to show that with an elastomeric gasket typically having a Shore A hardness of 70° a minimum contact pressure of 1.5 N/mm² is required. This contact pressure corresponds to an elastomeric gasket being compressed by 15 percent of its original thickness.

When a gasket is fabricated of elastomeric material, compressing one dimension of the gasket results in expansion of its other dimension, but the total volume of gasket material remains constant. For example, a 20% axial compression of the gasket thickness will cause a radial elongation of about 25%. Depending on the dimensions of the pipe flanges and that of the gasket, the radial elongation of the gasket 12 may cause portion 12c to be extruded into the pipe lumen. Projecting portion 12c can then be abraded by the flow of material being carried through the sanitary pipes.

This is shown in FIG. 4 where a conventional gasket 12 made of elastomeric material has a pre-compression axial thickness T. When the usual clamp (not shown) is made up to draw the pipe sections axially together gasket 12 is compressed by an amount t so that its final thickness is T−t. At the same time its radial dimension increases. Depending on the amount of compression, the amount of radial increase may cause a portion 12c of the gasket to be extruded into the lumen of the pipe. It is this portion 12c of the gasket that is exposed to the process stream being carried by the pipes.

To comply with sanitary requirements, sanitary piping systems are periodically subjected to high temperature steam sterilization. Under such conditions, gaskets tend to deteriorate. The deterioration leads to a lowering of elasticity, the gasket becomes stiff and cracks form. When the piping system is then used to carry a process stream a portion of the gasket surface 12c may erode so that some small particles thereof become detached and enter and contaminate the process stream.

While modern elastomeric materials are designed to resist deterioration under operating conditions, there needs to be some way of telling when a gasket has in fact deteriorated to the point where it contaminates the process stream. Unfortunately, the detection of miniscule portions of elastomeric material in the process stream has required exotic spectrographic equipment.

While systems have been employed were feromagnetic additives have been incorporated into the elastomeric compositions to allow for detection of particulates lost from gaskets or o-rings. Such additives, however, are not distinguishable from their surroundings if present in an environment which shields magnetometers or which would produce sufficient false positives to render such detection methods inoperable.

What is needed therefore is a method for improving the detection of fragmented sanitary seals and gaskets in applications where detection use of magnetometers are unsuitable.

SUMMARY OF THE INVENTION

One embodiment of the present invention provides a system for the detection of contaminant particulates in closed containers, the system comprising; a plurality of system components susceptible to degredation during the manufacture of container contents and filling of the closed containers, the system components susceptible to degradation comprising a radio opaque composition of matter; an x-ray source disposed proximate to a path of the closed container in a production line; an x-ray image intensifier whereby x-rays from the x-ray source are collected and an image is generated; a ccd camera whereby the x-ray image is digitized; a contaminated container rejection mechanism whereby closed containers having x-ray images with radio opaque portions are rejected as contaminated and removed from the production line.

Another embodiment of the present invention provides such a system wherein the radio opaque composition of matter comprises barium.

A further embodiment of the present invention provides such a system wherein the barium is barium sulfate.

Still another embodiment of the present invention provides such a system wherein the radio opaque composition of matter is a polymer.

A still further embodiment of the present invention provides such a system wherein the polymer further comprises a finely divided radio opaque powder.

Yet another embodiment of the present invention provides such a system wherein the finely divided radio opaque powder comprises barium sulfate and reduced iron.

One embodiment of the present invention provides an elastomeric material, the elastomeric material comprising: An elastomer matrix; A radio contrast disposed in the elastomeric matrix, the radio contrast being radio opaque at wavelengths not greater than 10 nm. 8. The elastomeric material of claim 7 wherein the elastomer matrix comprises an elastomer selected from the group of elastomers comprising ethylene propylene diene monomer (EPDM), buna rubber, fluoroelastomers, vinylidene fluoride, hexafluoropropylene, and combinations thereof.

Another embodiment of the present invention provides such an elastomeric material wherein the radio contrast comprises barium.

A further embodiment of the present invention provides such an elastomeric material wherein the barium is in the form of Barium sulfate.

Still another embodiment of the present invention provides such an elastomeric material wherein the Barium Sulfate is greater than 4% by weight to the polymer mixture A still further embodiment of the present invention provides such an elastomeric material wherein, the Barium Sulate is about approximately 7% of the elastomeric material by weight. 13. The elastomeric material of claim 9 wherein the radio contrast further comprises ferromagnetic powders.

Even another embodiment of the present invention provides such an elastomeric material wherein the ferromagnetic powders comprise iron filings.

One embodiment of the present invention provides a method for the detection of contaminants in closed containers in a production line, the method comprising: using radio opaque tracer disposed in components of a production line; exposing the closed containers to x-ray radiation from an x-ray source; creating an x-ray image of contents of the closed containers; analyzing the x-ray image for radio opaque regions; rejecting closed containers having a high degree of radio opacity in at least one portion of the x-ray image.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

BRIEF DESCRIPTION OF THE DRAWINGS

The foregoing and other objects and features of the present invention may become more apparent from a reading of the ensuing description together with the drawing in which:

FIG. 1 shows prior art sanitary pipe fittings equipped with flanges for receiving an O-ring sealing gasket;

FIGS. 2 and 3 show cross-section and plan views of a prior art gasket for use with the sanitary fittings of FIG. 1;

FIG. 4 shows a section through the joint between prior art sanitary fittings using the prior art gasket demonstrating a typical intrusion of a portion of the gasket into the pipe lumen;

DETAILED DESCRIPTION

Figures 5, 6:
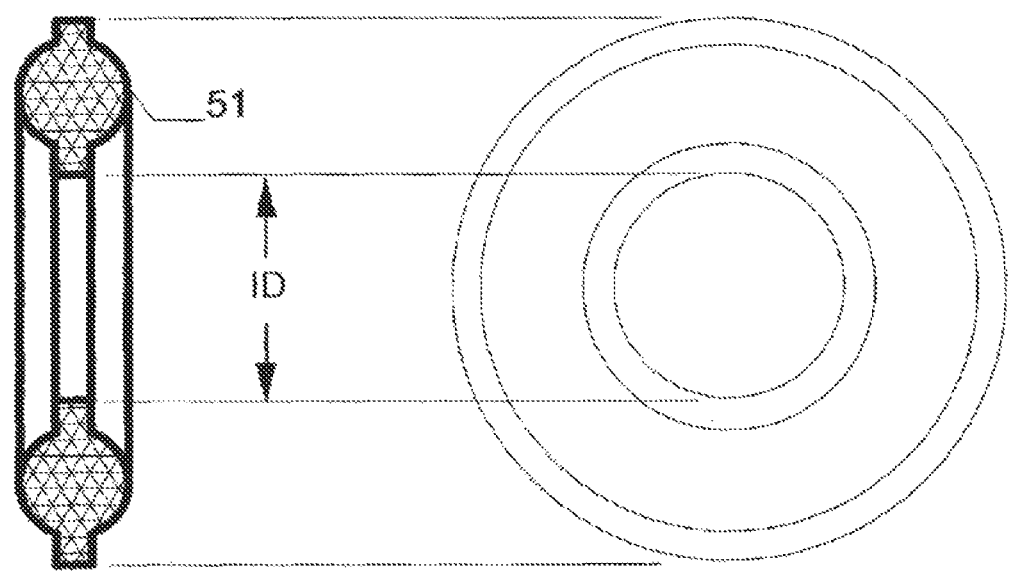
FIGS. 5 and 6 are cross-section and plan views of the improved gasket of the invention having distributed therethrough finely comminuted x-ray opaque material.

In one embodiment of the present invention, Gasket or o-rings such as those illustrated in FIG. 2 are manufactured from a composition of matter having a sufficient concentration of radio-opaque additive. Such detection is especially problematic where metal containers shield metal detection systems. However, in accordance with an aspect of the present invention, as shown in FIGS. 5 and 6, elastomeric gaskets or seals having incorporated radio-opaque material prior to being molded will enable detection of detached or separated fragments by either inexpensive metal detection equipment monitoring the process stream or by x-ray, or other radio detection devices similarly disposed along the process stream. FIGS. 5 and 6 show cross-sectional and plan views of elastomeric material formed as a molded O-ring gasket 51 having incorporated therein a finely divided x-ray opaque material, in one embodiment barium sulfate. In alternative embodiments, finely comminuted ferromagnetic particles may be incorporated into the composition to allow an additional means for identifying fragments of the elastomeric material.

An example of the proportion of elastomeric base material used in fabricating 50 durometer silicone rubber magnetic detectable gaskets is shown in the following table:

TABLE 1

| 50 Durometer Silicone Rubber with Comminuted Iron Powder | Batch = 60 lbs |
|---|---|
| Base: Elastosil 160 ® Silicone Rubber | Ingredient Weight |
| 35 durometer Elastosil 160 ® | 35 lbs |
| 75 durometer Elastosil 160 ® | 75 lbs |
| Curing Agent (2,4-dichlorobenzyl peroxide) | 375 grams |
| Pigment | 250 grams |
| Reduced Iron Powder | 25 lbs |
| Barium Sulfate | 10.27 lbs |

Proportions for x-ray opaque gaskets fabricated of ethylene propylene diene monomer (EPDM), buna rubber, and fluoroelastomers such as polytetrafluoroethylene (PTFE), Fluorinated ethylene propylene (FEP), Perfluoroalkoxy (PFA) Viton® or FKM 615A™ a dipolymer of vinylidene fluoride and hexafluoroproplyene often used as base elastomers for seals, spacers and gaskets employed in sanitary piping systems are similar. In embodiments employing a ferromagnetic additive as well as an X-ray opaque additive, the amount of reduced iron powder employed should be effective to trigger magnetic detectors monitoring the sanitary piping system while keeping the hardness of the cured elastomer in the range between 40 to 90 but in some embodiments, 50, as measured on the Shore A scale. An example of the threshold sensitivity often employed with magnetic detectors is that which can respond to the appearance of a metal ball 1.5 mm in diameter in the product stream.

X-ray opaque additives should be added in an effective concentration to allow for clean and unambiguous identification of debris in x-ray images. Such radio opaque additives, in some embodiments, can include insoluble salts of barium. In one embodiment Barium Sulfate particles are added in a concentration of greater than 4% by weight to the polymer mixture, while in other embodiments the concentration is about approximately 7%.

As noted above, in one embodiment, ferromagnetic materials like reduced iron may be added to the gasket material with the x-ray opaque material.

Containers to be inspected may include, but are not limited to closed containers such as trays, boxes, foils, films, and bags manufactured from metals and other ferromagnetic materials; or with metallic coatings, metalized coatings.

Figure 7:
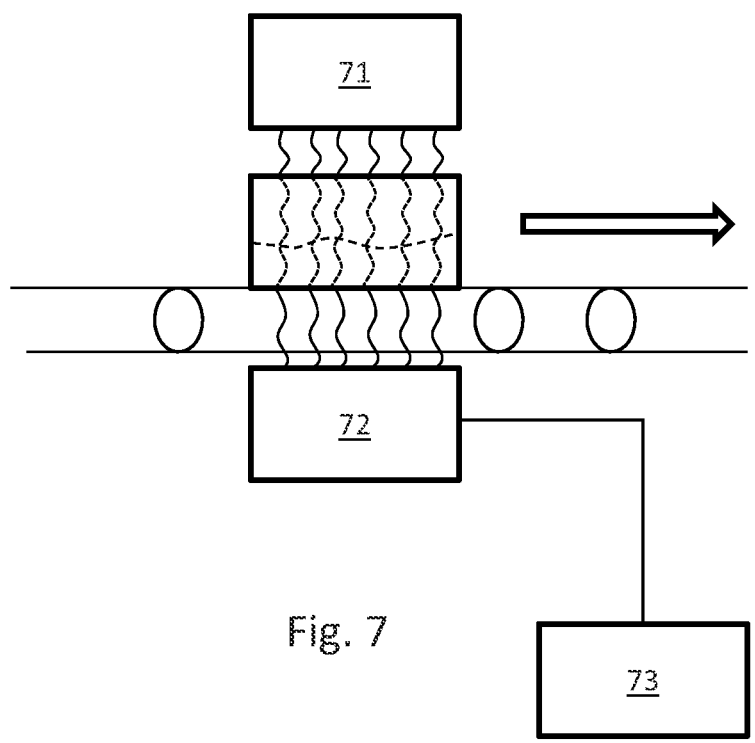
FIG. 7 is a schematic diagram of a x-ray detector installed in production line system.

FIG. 7 shows a common form of X-ray inspection system through which is disposed a section of sanitary piping carrying a product stream. X-ray generator 71 allows voltage and current to pass through an x-ray tube, resulting in the generation of X-rays. The x-ray generator 71 directs x-rays throughout the space within containers passing along a production line or conveyer. Contained within the containers are foodstuffs or other products dispensed from sanitary piping apparatus X-rays passing the contents of the container and are collected by an X-ray image intensifier or fluoroscope 72. If particles containing BaSO4 are present, the high absorption of the X-rays by the $BaSO_4$ additive will result in highly defined X-ray images of the particles. In one embodiment, images may be captured by CCD video cameras 73, and output to a graphic display.

Figure 8:
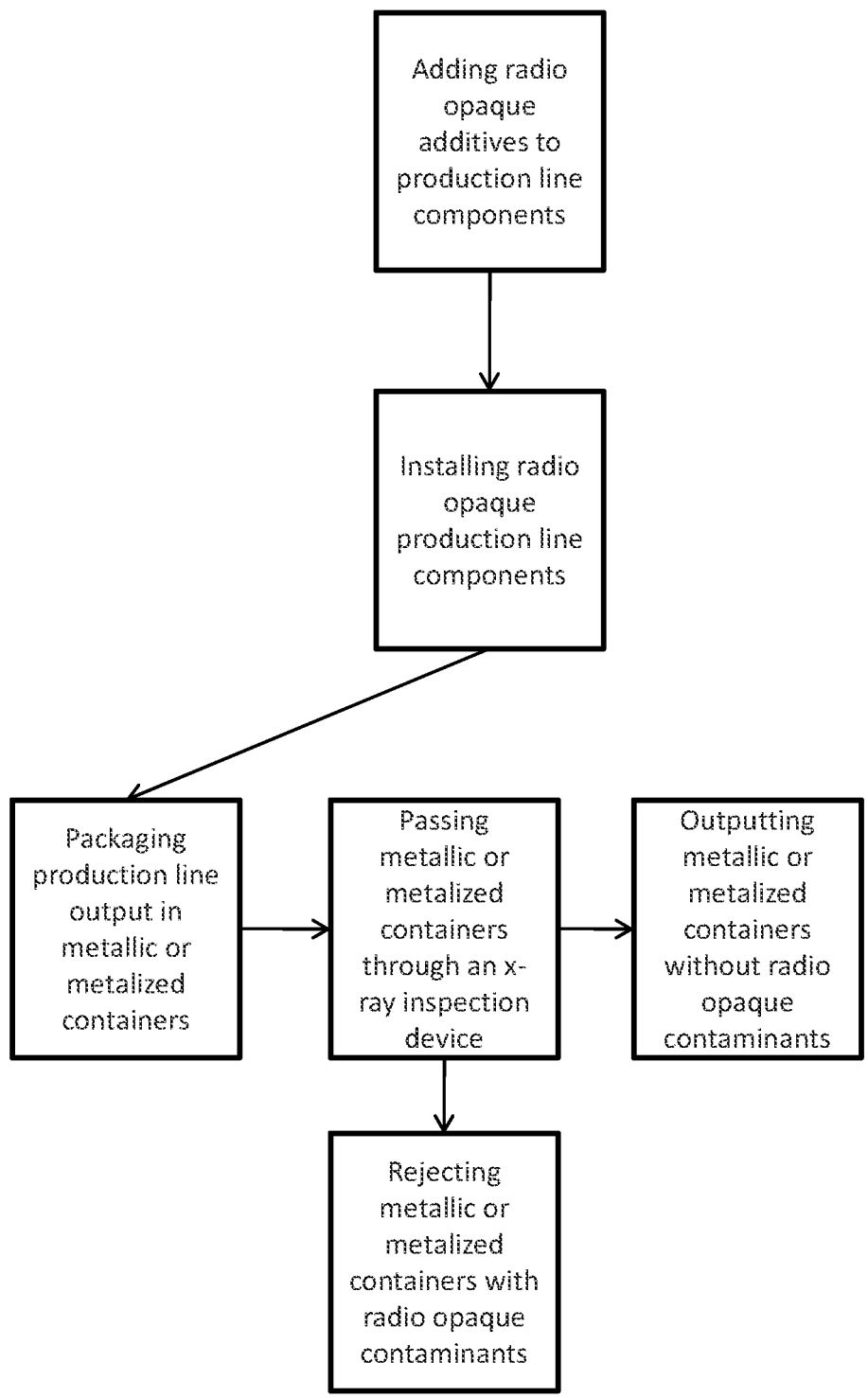
FIG. 8 is a flow chart of a method of x-ray detection installed in a production line system.

As illustrated in FIG. 8, one embodiment of the present invention includes a method for the detection of fragments from seals and o-rings in metal containers. In such an embodiment, radio opaque compounds are added to the elastomeric materials in the system during manufacture of elastomeric components, x-ray inspection devices are disposed at pre-defined points in the system including a final production line conveyer proximate to closed containers or piping. X-ray images are taken in real time of the contents of the linpassinge. Line contents are monitored for radio opaque fragments within the line. In one embodiment, the system may be programmed to detect opaque (white) shapes in X-ray images and reject or discard containers wherein such shapes are detected as contaminated.

The foregoing description of the embodiments of the invention has been presented for the purposes of illustration and description. Each and every page of this submission, and all contents thereon, however characterized, identified, or numbered, is considered a substantive part of this application for all purposes, irrespective of form or placement within the application. This specification is not intended to be exhaustive or to limit the invention to the precise form disclosed. Many modifications and variations are possible in light of this disclosure.

I claim:

1. A system for the detection of contaminant particulates in closed containers, said system comprising:
   a plurality of solid polymer gaskets comprising radio-opaque, barium-containing polymerized fluorinated hydrocarbon elastomers disposed in a production line of container contents and susceptible to degradation during the manufacture of said container contents and filling of said closed containers;
   an x-ray source disposed proximate to a path of said closed container in a production line;
   an x-ray image intensifier whereby x-rays from said x-ray source are collected and an image is generated;
   a ccd camera whereby said x-ray image is digitized;
   a contaminated container rejection mechanism whereby closed containers having x-ray images with radio opaque portions are rejected as contaminated and removed from said production line.

2. The system of claim 1, wherein said barium is barium sulfate.

3. The system of claim 1, wherein said radio opaque substance comprises a finely divided powder.

4. The system according to claim 3, wherein said finely divided radio opaque powder comprises barium sulfate and reduced iron.

5. A method for the detection of contaminants in closed containers in a production line, said method comprising:
   using radio opaque tracer disposed in solid polymerized fluorinated hydrocarbon gaskets disposed in a production line;
   exposing said closed containers to x-ray radiation from an x-ray source;
   creating an x-ray image of contents of said closed containers;
   analyzing said x-ray image for radio opaque regions indicative of fragments of said gaskets;
   rejecting closed containers having a high degree of radio opacity in at least one portion of said x-ray image.

* * * * *